(12) United States Patent
Iwasaki et al.

(10) Patent No.: US 12,343,213 B2
(45) Date of Patent: Jul. 1, 2025

(54) ULTRASOUND DIAGNOSIS APPARATUS, IMAGE PROCESSING APPARATUS, AND COMPUTER PROGRAM PRODUCT

(71) Applicant: CANON MEDICAL SYSTEMS CORPORATION, Otawara (JP)

(72) Inventors: Ryosuke Iwasaki, Otawara (JP); Hiroki Takahashi, Nasushiobara (JP); Tomohisa Imamura, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 589 days.

(21) Appl. No.: 17/711,250

(22) Filed: Apr. 1, 2022

(65) Prior Publication Data

US 2022/0313221 A1  Oct. 6, 2022

(30) Foreign Application Priority Data

Apr. 5, 2021 (JP) .................. 2021-064287

(51) Int. Cl.
*A61B 8/00* (2006.01)
*A61B 8/06* (2006.01)
(Continued)

(52) U.S. Cl.
CPC .............. *A61B 8/5269* (2013.01); *A61B 8/06* (2013.01); *G01S 7/52077* (2013.01); *G06T 11/008* (2013.01); *G06T 2210/41* (2013.01)

(58) Field of Classification Search
CPC ..... A61B 8/5223; A61B 8/5207; A61B 8/488; A61B 8/06; A61B 8/0883; A61B 8/4488;
(Continued)

(56) References Cited

U.S. PATENT DOCUMENTS 5,653,234 A * 8/1997 Kim ..................... G01S 7/52077
600/455
6,511,426 B1 * 1/2003 Hossack ............. G01S 15/8995
600/437
(Continued)

FOREIGN PATENT DOCUMENTS

JP  2006087757 A *  4/2006
JP  2020-114294 A    7/2020
(Continued)

OTHER PUBLICATIONS

Machine translation of JP2006087757A from Google patents (Year: 2006).*

(Continued)

*Primary Examiner* — Aaron W Carter
*Assistant Examiner* — Courtney Joan Nelson
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to receive an input of first ultrasound data and to output second ultrasound data. The processing circuitry is configured to reconstruct third ultrasound data on the basis of amplitude information in the second ultrasound data and phase information in the first ultrasound data. The processing circuitry is configured to perform a process that uses amplitude information and phase information in the third ultrasound data.

13 Claims, 7 Drawing Sheets

(51) Int. Cl.
*G01S 7/52* (2006.01)
*G06T 11/00* (2006.01)

(58) Field of Classification Search
CPC ... A61B 5/7264; A61B 5/7267; A61B 8/5246; A61B 2090/378; A61B 8/5269; G06T 2207/10132; G06T 2207/20081; G06T 7/0012; G06T 2207/20084; G06T 2207/30048; G06T 2207/30004; G06T 2207/10136; G06T 2210/41; G06T 2207/30101; G06T 5/70; G06T 2207/30104; G06T 5/50; G06T 5/60; G06T 11/008; G06N 3/045; G06N 3/08; G06N 20/00; G06N 3/0464; G06N 3/02; G06V 10/82; G06V 2201/03; G06V 10/30; G06F 30/27; G01S 7/52077
See application file for complete search history.

(56) References Cited

U.S. PATENT DOCUMENTS

| | | | | |
|---|---|---|---|---|
| 2013/0109968 A1* | 5/2013 | Azuma | .................. | A61B 8/145 600/447 |
| 2015/0324957 A1* | 11/2015 | Honjo | .................. | A61B 8/5246 600/447 |
| 2020/0281570 A1 | 9/2020 | Sato et al. | | |

FOREIGN PATENT DOCUMENTS

| | | | | |
|---|---|---|---|---|
| JP | 2020-114295 A | | 7/2020 | |
| WO | WO-2018127498 A1 * | | 7/2018 | ........... A61B 5/7267 |

OTHER PUBLICATIONS

G. Dong, Y. Ma and A. Basu, "Feature-Guided CNN for Denoising Images From Portable Ultrasound Devices," in IEEE Access, vol. 9, pp. 28272-28281, 2021, doi: 10.1109/ACCESS.2021.3059003 (Year: 2021).*

Japanese Notice of Reasons for Refusal issued Sep. 17, 2024 in Japanese Patent Application No. 2021-064287, 2 pgs.

* cited by examiner

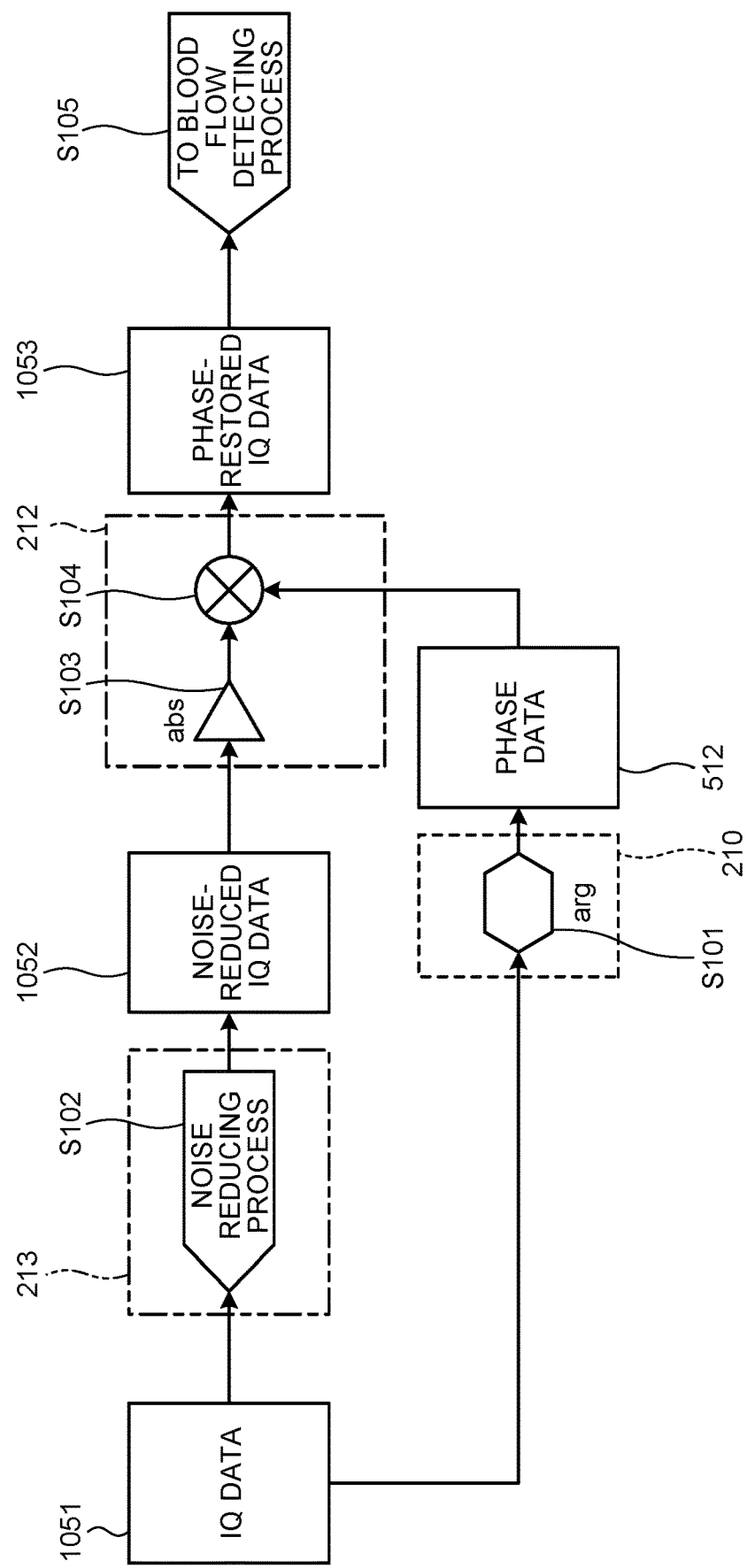

ULTRASOUND DIAGNOSIS APPARATUS, IMAGE PROCESSING APPARATUS, AND COMPUTER PROGRAM PRODUCT

CROSS-REFERENCE TO RELATED APPLICATIONS

This application is based upon and claims the benefit of priority from Japanese Patent Application No. 2021-064287, filed on Apr. 5, 2021; the entire contents of which are incorporated herein by reference.

FIELD

Embodiments described herein relate generally to an ultrasound diagnosis apparatus, an image processing apparatus, and a computer program product.

BACKGROUND

Conventionally, a technique is known by which an ultrasound diagnosis apparatus is configured to perform various types of processes such as a noise reducing process and a blood flow detecting process while using amplitude information and phase information included in ultrasound data obtained from a received reflected wave.

However, these processes that use both the amplitude information and the phase information cannot be performed after a process in which the phase information of the reflected wave is lost or altered. Accordingly, in some situations, it is not possible to efficiently perform multiple processes in combination.

BRIEF DESCRIPTION OF THE DRAWINGS

FIG. 8 is a chart illustrating an example of a flow in a process of generating the phase-restored IQ data according to the second embodiment.

DETAILED DESCRIPTION

An ultrasound diagnosis apparatus described in the following embodiments includes processing circuitry. The processing circuitry is configured to receive an input of first ultrasound data and to output second ultrasound data. The processing circuitry is configured to reconstruct third ultrasound data on the basis of amplitude information in the second ultrasound data and phase information in the first ultrasound data. The processing circuitry is configured to perform a process that uses amplitude information and phase information in the third ultrasound data.

Exemplary embodiments of an ultrasound diagnosis apparatus, an image processing apparatus, and a computer program product will be explained in detail below, with reference to the accompanying drawings.

First Embodiment

Figure 1:
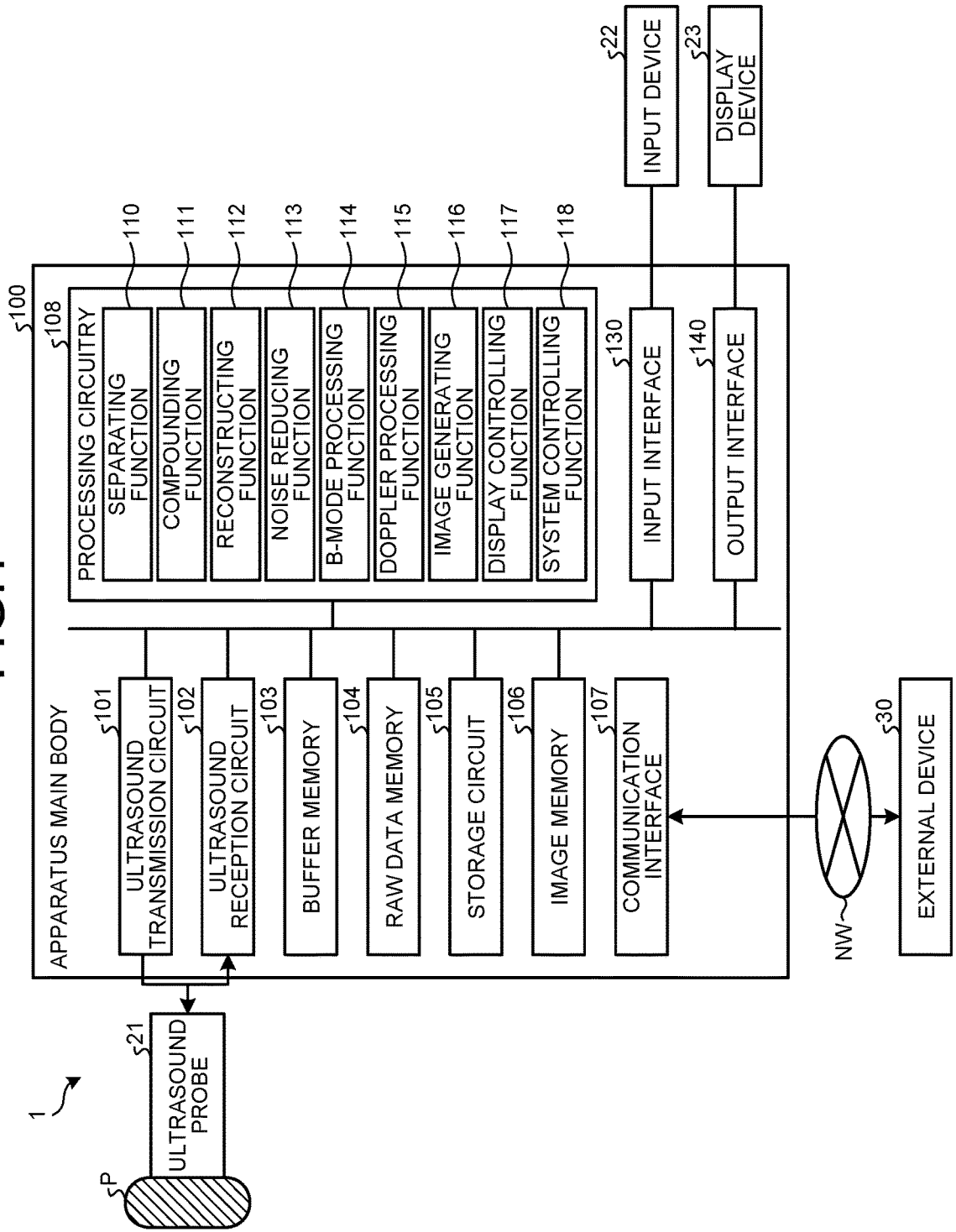
FIG. 1 is a block diagram illustrating an example of an ultrasound diagnosis apparatus according to a first embodiment.

FIG. 1 is a block diagram illustrating an example of an ultrasound diagnosis apparatus 1 according to a first embodiment. As illustrated in FIG. 1, the ultrasound diagnosis apparatus 1 includes an apparatus main body 100, an ultrasound probe 21, an input device 22, and a display device 23. Further, the apparatus main body 100 is connected to an external device 30 via a network NW.

For example, the ultrasound probe 21 includes a plurality of elements such as piezoelectric transducer elements. The plurality of elements are configured to generate an ultrasound wave on the basis of a drive signal supplied from an ultrasound transmission circuit 101 included in the apparatus main body 100. Further, the ultrasound probe 21 is configured to receive a reflected wave arriving from an examined subject (hereinafter, "patient") P and to convert the reflected wave into an electrical signal. Further, the ultrasound probe 21 includes, for example, a matching layer provided for the piezoelectric transducer elements and a backing material that prevents ultrasound waves from propagating rearward from the piezoelectric transducer elements, or the like. The ultrasound probe 21 is detachably connected to the apparatus main body 100.

When an ultrasound wave is transmitted from the ultrasound probe 21 to the patient P, the transmitted ultrasound wave is repeatedly reflected on a surface of discontinuity of acoustic impedances at a tissue in the body of the patient P and is received as a reflected-wave signal by the plurality of elements included in the ultrasound probe 21. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving objects with respect to the ultrasound wave transmission direction. Further, the ultrasound probe 21 is configured to output the reflected-wave signal to an ultrasound reception circuit 102 included in the apparatus main body 100.

In the present embodiment, it is assumed that the ultrasound probe 21 is a one-dimensional array probe in which the plurality of ultrasound transducer elements are arranged along a predetermined direction; however, the present disclosure is not limited to this example. When being configured to be able to obtain volume data, the ultrasound probe 21 may be a two-dimensional array probe (a probe in which the plurality of ultrasound transducer elements are arranged in a two-dimensional matrix formation) or may be a mechanical four-dimensional (4D) probe (a probe capable of performing an ultrasound scan while mechanically swinging an ultrasound transducer element array in a direction orthogonal to the array direction).

For example, the input device 22 is realized by using an input means such as a mouse, a keyboard, a button, a panel switch, a touch command screen, a foot switch, a trackball, a joystick, and/or the like. The input device 22 is configured to receive various types of setting requests from an operator of the ultrasound diagnosis apparatus 1 and to transfer the received various types of setting requests to the apparatus main body 100.

For example, the display device 23 is configured to display a Graphical User Interface (GUI) used by the operator of the ultrasound diagnosis apparatus 1 to input the various types of setting requests via the input device 22 and is configured to display an ultrasound image represented by ultrasound image data generated by the apparatus main body 100 or the like. The display device 23 is realized by using a liquid crystal display monitor, an Organic Light Emitting Diode (OLED) monitor, or the like.

The apparatus main body 100 is configured to generate the ultrasound image data on the basis of the reflected-wave signal received by the ultrasound probe 21. The apparatus main body 100 is capable of generating two-dimensional ultrasound image data, on the basis of reflected-wave data corresponding to a two-dimensional region of the patient P and being received by the ultrasound probe 21. Further, the apparatus main body 100 is capable of generating three-dimensional ultrasound image data on the basis of reflected-wave data corresponding to a three-dimensional region of the patient P and being received by the ultrasound probe 21.

As illustrated in FIG. 1, the apparatus main body 100 includes the ultrasound transmission circuit 101, the ultrasound reception circuit 102, a buffer memory 103, a raw data memory 104, a storage circuit 105, an image memory 106, a communication interface 107, processing circuitry 108, an input interface 130, and an output interface 140.

Under control of the processing circuitry 108, the ultrasound transmission circuit 101 is configured to cause the ultrasound probe 21 to transmit the ultrasound wave. For example, the ultrasound transmission circuit 101 includes a trigger generating circuit, a delay circuit, and a pulser circuit, or the like (not illustrated). The trigger generating circuit is configured to repeatedly generate a trigger pulse used for forming a transmission ultrasound wave at a predetermined rate frequency fr Hz (the cycle: 1/fr seconds). Further, the delay circuit is configured to apply a delay time period that is required to converge the ultrasound wave into the form of a beam for each channel and to determine transmission directionality, to each of the trigger pulses. The pulser circuit is configured to apply a drive pulse to the ultrasound probe 21 with timing based on the trigger pulses.

The ultrasound reception circuit 102 is configured to generate the reflected-wave data on the basis of the reflected-wave signal received by the ultrasound probe 21. The reflected-wave data is an example of the first ultrasound data according to the present embodiment. Further, the ultrasound reception circuit 102 is configured to store the generated reflected-wave data into the buffer memory 103.

More specifically, the reflected wave of the ultrasound wave transmitted by the ultrasound probe 21 reaches the piezoelectric transducer elements provided inside the ultrasound probe 21 and is subsequently converted at the piezoelectric transducer elements from mechanical vibration into the electrical signal (the reflected-wave signal) so as to be input to the ultrasound reception circuit 102. The ultrasound reception circuit 102 includes, for example, a pre-amplifier, an Analog-to-Digital (A/D) converter, a quadrature detection circuit, and the like and is configured to generate the reflected-wave data by performing various types of processes on the reflected-wave signal received by the ultrasound probe 21.

The pre-amplifier is configured to amplify the reflected-wave signal for each of the channels and to adjust a gain (a gain correction). The A/D converter is configured to convert the gain-corrected reflected-wave signal into a digital signal by performing an A/D conversion on the gain-corrected reflected-wave signal. The quadrature detection circuit is configured to convert the reflected-wave signal resulting from the A/D conversion into an In-phase signal (an I signal) and a Quadrature-phase signal (a Q signal) in a baseband.

Further, the quadrature detection circuit is configured to store the I signal and the Q signal into the buffer memory 103 as the reflected-wave data. In the following sections, the I signal and the Q signal may collectively be referred to as IQ signals. Further, because the IQ signals is the digital data resulting from the A/D conversion, the IQ signals may be referred to as IQ data. The IQ data is complex signal data including amplitude information and phase information.

The ultrasound reception circuit 102 is configured to generate two-dimensional reflected-wave data from a two-dimensional reflected-wave signal received by the ultrasound probe 21. Alternatively, the ultrasound reception circuit 102 may generate three-dimensional reflected-wave data from a three-dimensional reflected-wave signal received by the ultrasound probe 21.

The buffer memory 103 is configured to at least temporarily store therein the reflected-wave data (the TQ data) generated by the ultrasound reception circuit 102. For example, the buffer memory 103 is configured to store therein the reflected-wave data corresponding to a number of frames or the reflected-wave data corresponding to a number of volumes. For example, under control of the ultrasound reception circuit 102, the buffer memory 103 is configured to store therein the reflected-wave data corresponding to a predetermined number of frames. Further, when the ultrasound reception circuit 102 has newly generated reflected-wave data corresponding to one frame while the buffer memory 103 has stored therein the reflected-wave data corresponding to the predetermined number of frames, the buffer memory 103 is configured, under control of the ultrasound reception circuit 102, to discard the reflected-wave data corresponding to one frame that was generated earliest and to store therein the reflected-wave data corresponding to the one frame that was newly generated. For example, the buffer memory 103 is realized by using a semiconductor memory element such as a Random Access Memory (RAM) or a flash memory. Further, the reflected-wave data corresponding to one frame and being generated by the ultrasound reception circuit 102 is reflected-wave data corresponding to one acquisition frame. The buffer memory 103 is an example of a storage unit according to the present embodiment. Alternatively, the buffer memory 103 may be referred to as a temporary storage unit.

The raw data memory 104 is configured to store therein various types of data such as B-mode data and Doppler data generated by the processing circuitry 108 (explained later). The raw data memory 104 is realized by using a semiconductor memory element such as a RAM or a flash memory, or a hard disk, an optical disk, or the like.

For example, the storage circuit 105 is realized by using a magnetic or optical storage medium, a semiconductor memory element such as a flash memory, a storage medium that can be read by a processor such as a hard disk or an optical disk, or the like. The storage circuit 105 has stored therein programs and various types of data used for realizing the ultrasound transmission/reception. For example, the programs and the various types of data may be stored in the storage circuit 105 in advance. Alternatively, the programs and the various types of data may be distributed as being stored in a non-transitory storage medium, for example, so as to be installed in the storage circuit 105 as being read from the non-transitory storage medium. In an example, the storage circuit 105 may serve as an example of a storage unit according to the present embodiment.

The image memory 106 is configured to store therein various types of image data generated by the processing circuitry 108. For example, the image memory 106 is realized by using a semiconductor memory element such as a RAM or a flash memory, or a hard disk, an optical disk, or the like. In an example, the raw data memory 104 and the image memory 106 may be integrated together as a single memory.

The communication interface 107 is connected to the external device 30 via the network NW, for example, and is configured to perform data communication with the external device 30.

For example, the external device 30 is a workstation configured to perform post-processing on various types of data generated by the ultrasound diagnosis apparatus 1 and to perform processes such as displaying ultrasound image data. For example, the external device 30 includes processing circuitry such as a processor, as well as a storage device and a display device. Alternatively, the external device 30 may be a tablet device or the like.

The input interface 130 is configured to receive various types of instructions from the operator via the input device 22. The input interface 130 is connected to the processing circuitry 108 via a bus, for example, and is configured to convert operation instructions input by the operator into electrical signals and to output the electrical signals to the processing circuitry 108. In this situation, the input interface 130 does not necessarily have to be connected to physical operation component parts such as a mouse, a keyboard, and/or the like. For instance, possible examples of the input interface include a circuit configured to receive an electrical signal corresponding to an operation instruction and being input thereto from an external input device provided separately from the ultrasound diagnosis apparatus 1 and configured to output the electrical signal to the processing circuitry 108.

For example, the output interface 140 is configured to output electrical signals received from the processing circuitry 108 to the outside. For example, the output interface 140 is connected to the processing circuitry 108 via a bus and is configured to output an electrical signal received from the processing circuitry 108 to the display device 23.

The processing circuitry 108 is a processor configured to realize functions corresponding to programs, by reading and executing the programs from the storage circuit 105. The processing circuitry 108 according to the present embodiment includes a separating function 110, a compounding function 111, a reconstructing function 112, a noise reducing function 113, a B-mode processing function 114, a Doppler processing function 115, an image generating function 116, a display controlling function 117, and a system controlling function 118.

The separating function 110 is an example of a separating unit. The compounding function 111 is an example of a first processing unit and a compounding processing unit. The reconstructing function 112 is an example of a reconstructing unit. The noise reducing function 113 is an example of a second processing unit and a noise reducing unit. The B-mode processing function 114 is an example of a B-mode processing unit. The Doppler processing function 115 is an example of a Doppler processing unit. The image generating function 116 is an example of an image generating unit. The display controlling function 117 is an example of a display controlling unit. The system controlling function 118 is an example of a system controlling unit.

In this situation, for example, processing functions of the constituent elements of the processing circuitry 108, namely, the separating function 110, the compounding function 111, the reconstructing function 112, the noise reducing function 113, the B-mode processing function 114, the Doppler processing function 115, the image generating function 116, the display controlling function 117, and the system controlling function 118, are stored in the storage circuit 105 in the form of computer-executable programs. For example, the processing circuitry 108 is configured to realize the functions corresponding to the programs by reading and executing the programs from the storage circuit 105. In other words, the processing circuitry 108 that has read the programs has the functions illustrated within the processing circuitry 108 in FIG. 1. Although the example was explained with reference to FIG. 1 in which the single processor realizes the processing functions implemented by the separating function 110, the compounding function 111, the reconstructing function 112, the noise reducing function 113, the B-mode processing function 114, the Doppler processing function 115, the image generating function 116, the display controlling function 117, and the system controlling function 118, it is also acceptable to structure the processing circuitry 108 by combining together a plurality of independent processors so that the functions are realized as a result of the processors executing the programs. Further, although the example was explained with reference to FIG. 1 in which the single storage circuit (i.e., the storage circuit 105) stores therein the programs corresponding to the processing functions, it is also acceptable to provide a plurality of storage circuits in a distributed manner, so that the processing circuitry 108 reads a corresponding program from each of the individual storage circuits.

In the above description, the example was explained in which the "processor" is configured to read and execute the programs corresponding to the functions from the storage circuit; however, possible embodiments are not limited to this example. The term "processor" denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). When the processor is a CPU, for example, the processor is configured to realize the functions by reading and executing the programs saved in the storage circuit 105. In contrast, when the processor is an ASIC, instead of having the programs saved in the storage circuit 105, the functions are directly incorporated in the circuit of the processor as a logic circuit. Further, the processors of the present embodiment do not each necessarily have to be structured as a single circuit. It is also acceptable to structure one processor by combining together a plurality of independent circuits so as to realize the functions thereof. Further, it is also acceptable to integrate two or more of the constituent elements illustrated in FIG. 1 into one processor so as to realize the functions thereof.

Figure 2:
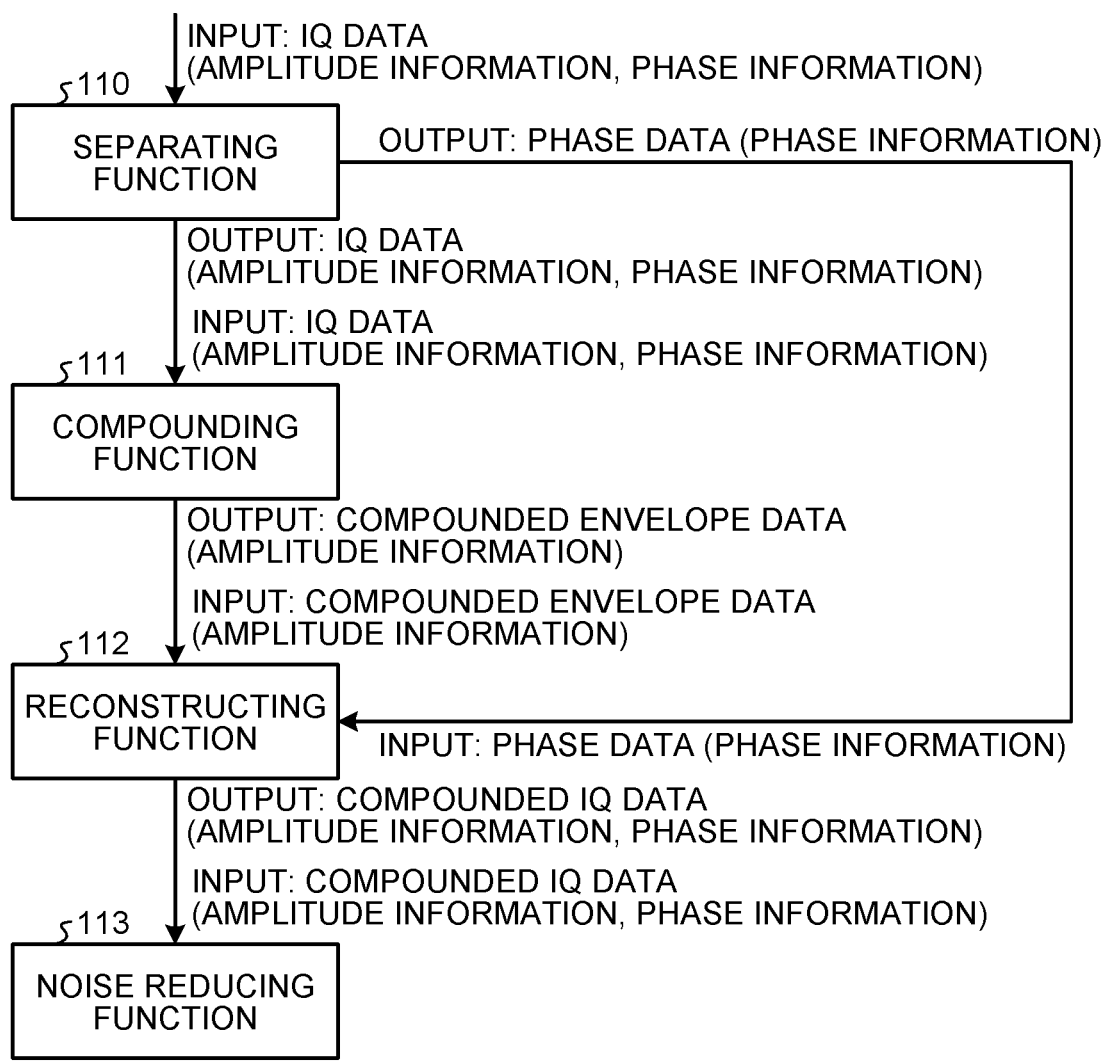
FIG. 2 is a chart illustrating an example of a relationship among functions related to generating compounded IQ data according to the first embodiment.

FIG. 2 is a chart illustrating an example of a relationship among functional units related to generating compounded IQ data according to the first embodiment.

The separating function 110 is configured to separate phase data including the phase information from the IQ data stored in the buffer memory 103. More specifically, as illustrated in FIG. 2, upon receipt of an input of the IQ data including the amplitude information and the phase information, the separating function 110 is configured to output the phase data including the phase information and IQ data including the amplitude information and the phase information.

The compounding function 111 is configured to receive an input of the IQ data and to output compounded envelope data. More specifically, the compounding function 111 is configured to generate the compounded envelope data by generating envelope data from IQ data corresponding to a plurality of frames and compounding the envelope data. In the explanation of the present embodiment, to distinguish the two types of data, the data before the compounding process will be referred to as "envelope data", whereas the data after the compounding process will be referred to as "compounded envelope data". Alternatively, the data before and after the compounding process may simply be referred to as envelope data collectively. The envelope data and the compounded envelope data include the amplitude information, but do not include the phase information. The compounded envelope data is an example of the second ultrasound data according to the present embodiment.

On the basis of the amplitude information in the compounded envelope data and the phase information in the IQ data, the reconstructing function 112 is configured to reconstruct compounded IQ data including the amplitude information and the phase information. In the present embodiment, because the phase information of the IQ data is included in the phase data separated by the separating function 110, the reconstructing function 112 is configured to reconstruct the compounded IQ data by using the amplitude information in the compounded envelope data and the phase information in the phase data.

Similarly to the IQ data, the compounded IQ data has a data structure including both the amplitude information and the phase information. Generally speaking, when a compounding process is performed on IQ data, phase information is lost. In contrast, in the compounded IQ data according to the present embodiment, because the phase information is added by the reconstructing function 112, the phase information is held even though the compounding process has been performed. The compounded IQ data is an example of the third ultrasound data according to the present embodiment.

On the basis of the amplitude information and the phase information in the compounded IQ data, the noise reducing function 113 is configured to generate noise-reduced IQ data having a Signal-to-Noise (SN) ratio higher than that of the compounded IQ data.

The noise-reduced IQ data is an example of the fourth ultrasound data according to the present embodiment. Further, the noise reducing process performed by the noise reducing function 113 is an example of a process that uses the amplitude information and the phase information in the compounded IQ data according to the present embodiment.

The amplitude information in the compounded IQ data is derived from the compounded envelope data. The phase information in the compounded IQ data is derived from the phase information in the IQ data stored in the buffer memory 103. In other words, by using the compounded IQ data, the noise reducing function 113 is able to perform the noise reducing process by using the amplitude information in the compounded envelope data and the phase information derived from the IQ data prior to the time when the phase information was lost due to the compounding process.

Figure 3:
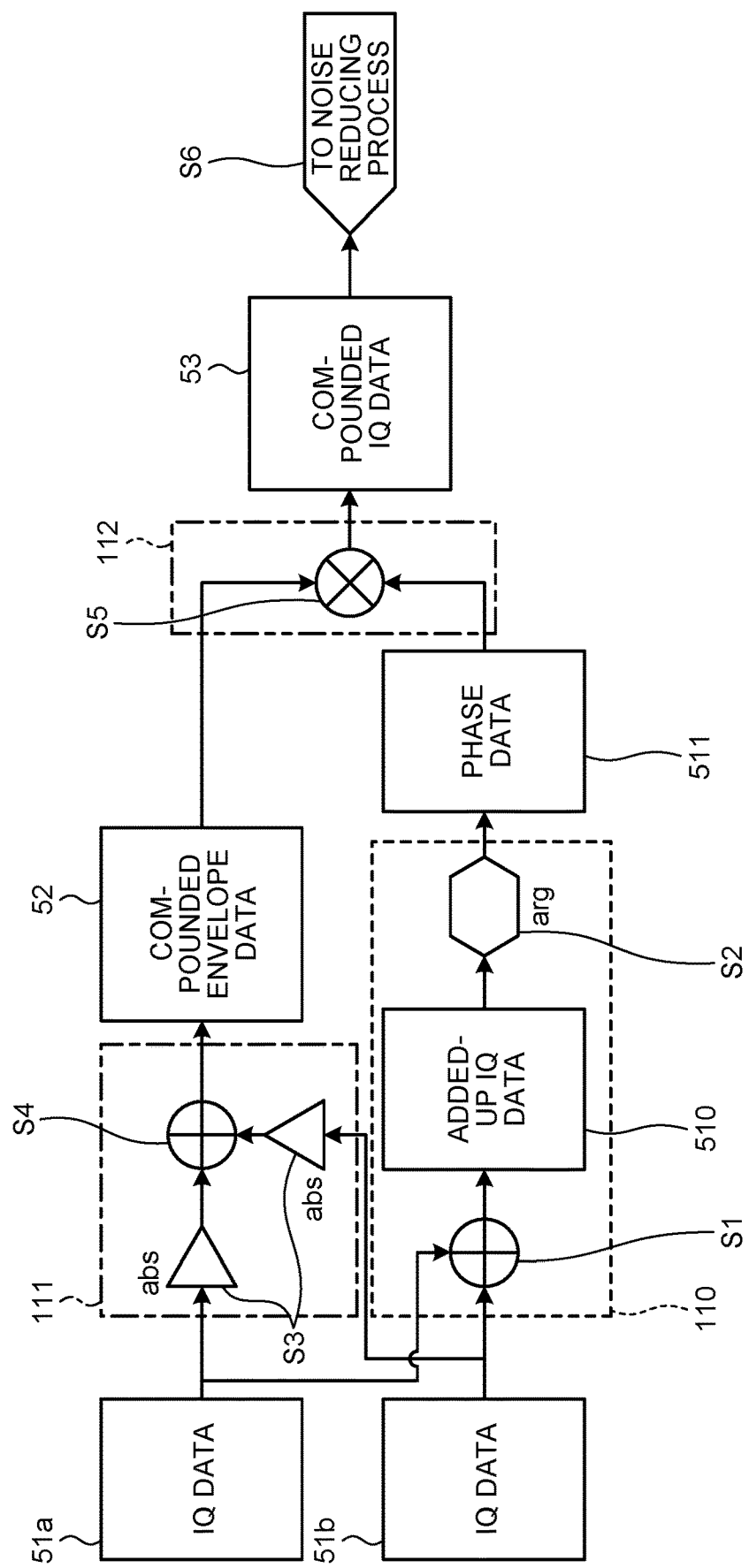
FIG. 3 is a chart illustrating an example of a flow in a process of generating the compounded IQ data according to the first embodiment.

Next, a flow in processes performed by the separating function 110, the compounding function 111, and the reconstructing function 112 will be explained with reference to FIG. 3. FIG. 3 is a chart illustrating an example of a flow in the process of generating compounded IQ data 53 according to the first embodiment. In FIG. 3, processes performed by the separating function 110, the compounding function 111, and the reconstructing function 112 are indicated in the enclosures of the broken-line boxes.

Each of the pieces of IQ data 51a and 51b in FIG. 3 is a piece of IQ data corresponding to one frame. In the following sections, when not being distinguished from each other, the pieces of IQ data 51a and 51b will be simply referred to as IQ data 51. Further, although the pieces of IQ data 51a and 51b corresponding to two frames serve as processing targets in FIG. 3, it is also acceptable to use, as processing targets, the pieces of IQ data 51a and 51b corresponding to three or more frames.

As indicated in Expression (1), the separating function 110 generates added-up IQ data 510, by adding together the pieces of IQ data 51a and 51b corresponding to the plurality of frames (step S1). Each of the pieces of IQ data 51a and 51b and the added-up IQ data 510 is complex signal data having a real part and an imaginary part.

$$IQ0+IQ1 \tag{1}$$

In Expression (1), "IQ0" denotes the piece of IQ data 51a, whereas "IQ1" denotes the piece of IQ data 51b.

Further, from the added-up IQ data 510, the separating function 110 extracts an argument of complex "/IQ" of the complex number as the phase information (step S2). The separating function 110 outputs phase data 511 including the extracted phase information.

Further, as indicated in Expression (2), the compounding function 111 generates the envelope data corresponding to the pieces of IQ data 51a and 51b, by extracting absolute values of the pieces of IQ data 51a and 51b corresponding to the plurality of frames (step S3). By calculating an arithmetic mean of the extracted plurality of absolute values (step S4), the compounding function 111 generates one piece of compounded envelope data 52. The absolute values of the IQ data 51 serve as an example of the amplitude information.

$$(abs(IQ0)+abs(IQ1))/2 \tag{2}$$

In the example in FIG. 3, because what is compounded is the pieces of IQ data 51a and 51b corresponding to the two frames, Expression (2) indicates that a result of adding together the absolute value of the piece of IQ data 51a and the absolute value of the piece of IQ data 51b is divided by 2. The divisor varies in accordance with the number of frames to be compounded.

As a result of the calculation presented in Expression (3), the reconstructing function 112 reconstructs the compounded IQ data 53, from the compounded envelope data 52 generated by the compounding function 111 and the phase data 511 generated by the separating function 110 (step S5).

$$abs\ IQ^*\cos(\angle IQ)+j^*abs\ IQ^*\sin(\angle IQ) \tag{3}$$

In Expression (3), the ∠IQ and the ∠IQ each denote the argument of complex of the complex number extracted from the added-up IQ data 510 by the separating function 110.

Subsequently, the compounded IQ data 53 is used in the noise reducing process performed by the noise reducing function 113 (step S6).

Figure 4:
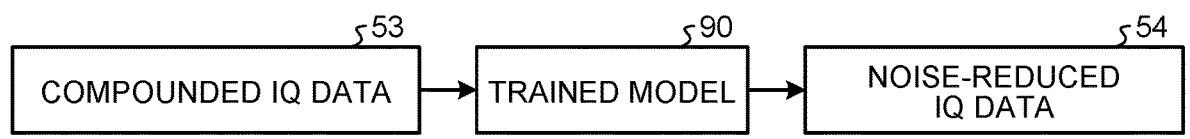
FIG. 4 is a chart illustrating an example of a noise reducing process performed by a trained model according to the first embodiment.

Next, details of the noise reducing function 113 will be explained, with reference to FIG. 4. FIG. 4 is a chart illustrating an example of a noise reducing process performed by using a trained model 90 according to the first embodiment. As illustrated in FIG. 4, upon receipt of the compounded IQ data 53, the trained model 90 is configured to output noise-reduced IQ data 54. The noise reducing function 113 obtains the noise-reduced IQ data 54, by inputting the compounded IQ data 53 to the trained model 90.

The trained model 90 is a trained model that has been trained while a plurality of pieces of input ultrasound data are kept in correspondence with a plurality of pieces of training ultrasound data. The training ultrasound data is data obtained by reducing a noise component of the input ultrasound data. A piece of input ultrasound data and a piece of training ultrasound data corresponding to the piece of input ultrasound data structure a set of learning data.

For example, the trained model 90 may be a trained model generated through deep learning such as a neural network or other machine learning schemes. As a method of the deep learning, it is possible to use a Deep Convolutional Neural Network (DCNN), a Convolutional Neural Network (CNN), or a Recurrent Neural Network (RNN); however, possible embodiments are not limited to these examples. For example, the trained model 90 is structured with a neural network and trained parameter data.

The trained model 90 may be stored in the storage circuit 105, for example. The noise reducing function 113 is configured to read the trained model 90 from the storage circuit 105 and to input the compounded IQ data 53 thereto. Alternatively, the trained model 90 may be incorporated in the noise reducing function 113.

Figure 5:
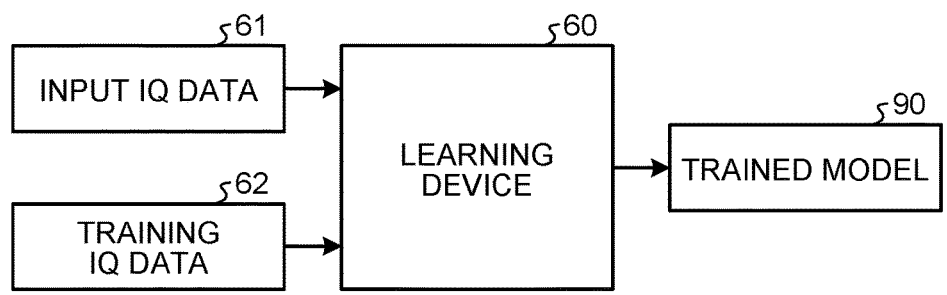
FIG. 5 is a chart illustrating an example of a method for generating the trained model according to the first embodiment.

FIG. 5 is a chart illustrating an example of a method for generating the trained model 90 according to the first embodiment. For example, the trained model 90 is generated by a learning device 60. The learning device 60 includes a machine learning model such as a DCNN. The learning device 60 is configured to generate the trained model 90, by performing a learning process (supervised learning) on the basis of input IQ data 61 and training IQ data 62 related to ultrasound examinations performed on mutually the same position of an examined subject. The training IQ data 62 is data obtained by reducing noise in the input IQ data 61. Further, although FIG. 5 illustrates the one set made up of the input IQ data 61 and the training IQ data 62, the learning device 60 is configured to learn a plurality of sets each made up of input IQ data 61 and training IQ data 62. The input IQ data 61 is an example of the input ultrasound data. The training IQ data 62 is an example of the training ultrasound data.

Alternatively, the ultrasound diagnosis apparatus 1 may include a learning function configured to generate the trained model 90. In that situation, the ultrasound diagnosis apparatus 1 may be referred to as the learning device 60.

Returning to the description of FIG. 1, the B-mode processing function 114 is configured to generate B-mode data from the noise-reduced IQ data 54. For example, the B-mode processing function 114 is configured to generate data (B-mode data) in which signal intensities are expressed with brightness levels, by performing a logarithmic compression process or the like on the noise-reduced IQ data 54. The B-mode processing function 114 is configured to store the generated B-mode data into the raw data memory 104, as B-mode raw data on two-dimensional ultrasound scanning lines (a raster). Alternatively, the B-mode raw data may be B-mode data on three-dimensional ultrasound scanning lines.

Alternatively, the separating function 110, the compounding function 111, the reconstructing function 112, and the noise reducing function 113 may be included in the B-mode processing function 114.

The Doppler processing function 115 is configured to generate data (Doppler data) obtained by extracting movement information based on the Doppler effect of a moving object in a Region Of Interest (ROI) set within a scanned region, by performing a frequency analysis on the IQ data 51 stored in the buffer memory 103. For example, the Doppler processing function 115 is capable of implementing a color doppler method that may be called a color flow mapping method. The Doppler processing function 115 is configured to store the generated Doppler data into the raw data memory 104, as Doppler raw data on two-dimensional ultrasound scanning lines. Alternatively, the Doppler raw data may be Doppler data on three-dimensional ultrasound scanning lines.

The image generating function 116 is configured to generate B-mode image data on the basis of the B-mode raw data generated by the B-mode processing function 114. Further, the image generating function 116 is configured to generate Doppler image data on the basis of the Doppler raw data generated by the Doppler processing function 115.

For example, the image generating function 116 is configured to generate two-dimensional ultrasound image data structured with pixels, by performing a raw-pixel conversion on the B-mode raw data and the Doppler raw data. For instance, examples of the ultrasound image data include B-mode image data, color Doppler image data, and Doppler waveform image data. In another example, the image generating function 116 may generate volume data by performing a raw-voxel conversion including an interpolation process that takes spatial position information into account, on the B-mode raw data stored in the raw data memory. In yet another example, the image generating function 116 may generate rendering image data or Multi Planar Reconstruction (MPR) image data by performing a rendering process, an MPR process, or the like, on various types of volume data. The image generating function 116 is configured to store the generated ultrasound image data into the image memory 106.

The display controlling function 117 is configured to cause the display device 23 to display ultrasound images based on the various types of ultrasound image data generated by the image generating function 116. Further, the display controlling function 117 may also cause the display device 23 to display the GUI used by the operator to input the various types of setting requests through the input device 22.

The system controlling function 118 is configured to govern and control operations of the entirety of the ultrasound diagnosis apparatus 1. For example, the system controlling function 118 is configured to control ultrasound scans, by controlling the ultrasound probe 21 via the ultrasound transmission circuit 101.

As explained above, the ultrasound diagnosis apparatus 1 according to the present embodiment includes the reconstructing function 112 configured to reconstruct the compounded IQ data 53, on the basis of the amplitude information in the compounded envelope data 52 generated from the IQ data 51 by the compounding function 111 and the phase information in the IQ data 51. Consequently, when the ultrasound diagnosis apparatus 1 according to the present embodiment is used, it is possible to perform the noise reducing process that uses the amplitude information and the phase information, even after the compounding process by which the phase information in the IQ data 51 is lost.

Further, the ultrasound diagnosis apparatus 1 according to the present embodiment is configured to generate the compounded envelope data 52, by compounding the IQ data 51 corresponding to the plurality of frames. Further, the ultrasound diagnosis apparatus 1 according to the present embodiment is configured to generate the noise-reduced IQ data 54 having a SN ratio higher than that of the compounded IQ data 53, on the basis of the amplitude information and the phase information in the compounded IQ data 53.

Generally speaking, a noise reducing process on IQ data would be performed with respect to each piece of IQ data corresponding to a single frame. For this reason, at the time of performing a process such as a compounding process where pieces of IQ data corresponding to a plurality of frames are integrated together, a noise reducing process would individually be performed with respect to the data corresponding to each frame, prior to the compounding process, on each of the pieces of IQ data corresponding to the plurality of frames to be compounded. After that, the compounding process would be performed on the noise-reduced IQ data corresponding to the plurality of frames. When this method is used, the processing load might increase in accordance with the number of frames to be compounded. For this reason, it is sometimes difficult to perform this type of noise reducing process during a real-time process of generating ultrasound image data while an ultrasound scan is performed on an examined subject. Further, because the phase information required by the noise reducing process would be lost by the compounding process, it is also difficult to perform the compounding process before the noise reducing process.

In contrast, the ultrasound diagnosis apparatus 1 according to the present embodiment is configured to reconstruct the compounded IQ data 53, on the basis of the amplitude information in the compounded envelope data 52 generated from the IQ data 51 corresponding to the plurality of frames and the phase information in the IQ data 51 corresponding to the plurality of frames. Further, the ultrasound diagnosis apparatus 1 according to the present embodiment is configured to perform the noise reducing process on the compounded IQ data 53. In other words, the ultrasound diagnosis apparatus 1 according to the present embodiment is configured to perform the noise reducing process on the compounded IQ data 53 obtained by putting together the plurality of frames to be compounded. Accordingly, even when the number of frames to be compounded has increased, it is possible to keep small the load in the noise reducing process. For this reason, even when both the compounding process and the noise reducing process are performed during a real-time process of generating ultrasound image data while an ultrasound scan is performed on the patient P, it is possible to enhance time resolution of the ultrasound image data.

Further, the ultrasound diagnosis apparatus 1 according to the present embodiment is configured to obtain the noise-reduced IQ data 54, by inputting the compounded IQ data 53 to the trained model 90. Generally speaking, the data structures of data to be input to the trained model 90 need to be uniform. For example, when the trained model 90 has been trained with input data having a data structure including amplitude information and phase information like the IQ data, it is necessary to input data including amplitude information and phase information to the trained model 90. Because the compounded IQ data 53 in the present embodiment has a data structure including the amplitude information and the phase information, similarly to the IQ data 51, when the ultrasound diagnosis apparatus 1 according to the present embodiment is used, it is also possible to apply the trained model 90 configured to perform a noise reducing process on individual pieces of IQ data, to the noise reducing process of the compounded IQ data 53.

Further, the ultrasound diagnosis apparatus 1 according to the present embodiment is configured to separate the phase data 511 including the phase information from the IQ data 51. By reconstructing the compounded IQ data 53 by using the amplitude information in the compounded envelope data 52 and the phase information in the phase data 511, the ultrasound diagnosis apparatus 1 according to the present embodiment is able to cause the compounded IQ data 53 to include the phase information before being lost in the compounding process.

In the present embodiment, the noise reducing process is used as an example of the process that uses the amplitude information and the phase information in the compounded IQ data 53; however, the process may be a process other than the noise reducing process as long as the process uses amplitude information and phase information. Further, in the present embodiment, the compounding process is used as an example of the process by which the phase information in the IQ data 51 is lost; however, the process may be a process other than the compounding process, as long as the phase information in the IQ data 51 is lost or altered by the process.

Second Embodiment

In the first embodiment above, the example was explained in which, after the compounding process by which the phase information is lost, the noise reducing process that uses the phase information is performed. In a second embodiment, an example will be explained in which, after a process having the possibility of altering phase information, a process that uses the phase information is performed.

Figure 6:
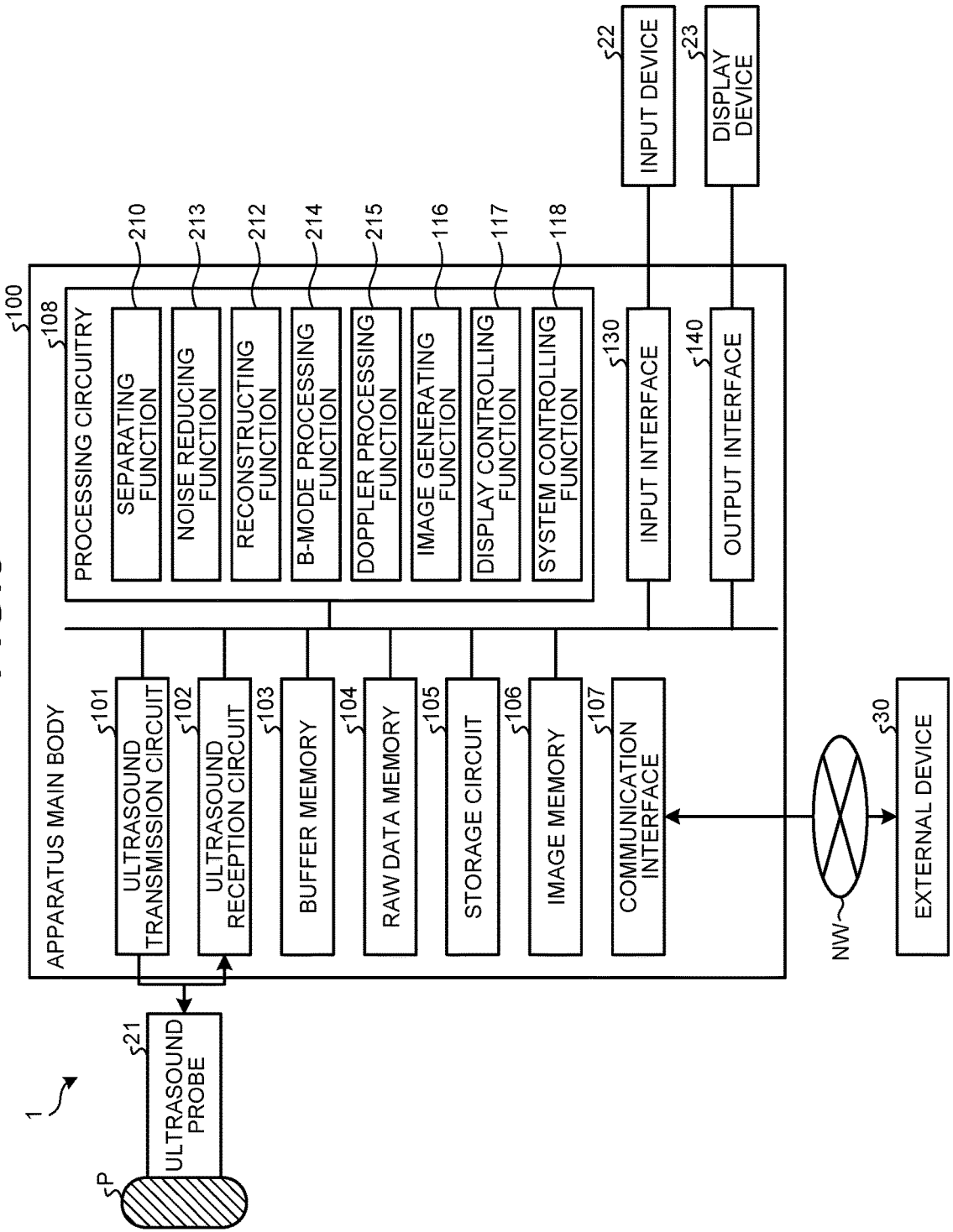
FIG. 6 is a block diagram illustrating an example of an ultrasound diagnosis apparatus according to a second embodiment.

FIG. 6 is a block diagram illustrating an example of the ultrasound diagnosis apparatus 1 according to the second embodiment. Similarly to the first embodiment explained with reference to FIG. 1, the ultrasound diagnosis apparatus 1 according to the present embodiment includes the apparatus main body 100, the ultrasound probe 21, the input device 22, and the display device 23 and is connected to the external device 30 via the network NW.

Further, similarly to the first embodiment, the apparatus main body 100 of the present embodiment includes the ultrasound transmission circuit 101, the ultrasound reception circuit 102, the buffer memory 103, the raw data memory 104, the storage circuit 105, the image memory 106, the communication interface 107, the processing circuitry 108, the input interface 130, and the output interface 140.

The processing circuitry 108 of the ultrasound diagnosis apparatus 1 according to the present embodiment includes a separating function 210, a noise reducing function 213, a reconstructing function 212, a B-mode processing function 214, a Doppler processing function 215, the image generating function 116, the display controlling function 117, and the system controlling function 118.

The separating function 210 is an example of a separating unit. The noise reducing function 213 is an example of a first processing unit and a noise reducing unit according to the present embodiment. The reconstructing function 212 is an example of a reconstructing unit. The B-mode processing function 214 is an example of a B-mode processing unit. The Doppler processing function 215 is an example of a second processing unit, a blood flow detecting unit, and a Doppler processing unit according to the present embodiment. The image generating function 116 is an example of an image generating unit. The display controlling function 117 is an example of a display controlling unit. The system controlling function 118 is an example of a system controlling unit.

Figure 7:
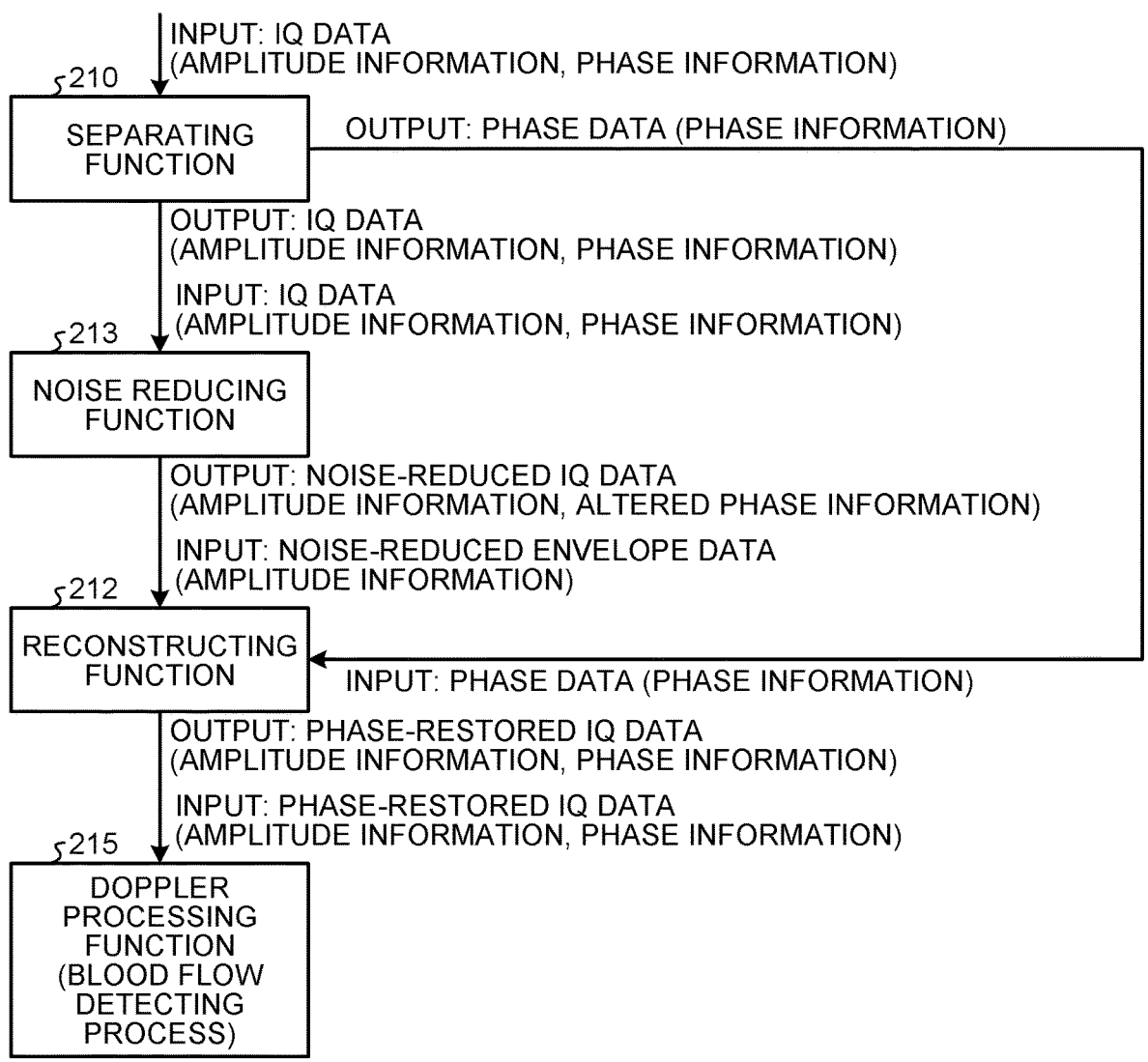
FIG. 7 is a chart illustrating an example of a relationship among functions related to generating phase-restored IQ data according to the second embodiment.

FIG. 7 is a chart illustrating an example of a relationship among functions related to generating phase-restored IQ data according to the second embodiment.

The separating function 210 is configured to separate phase data including phase information from the IQ data stored in the buffer memory 103. As illustrated in FIG. 7, upon receipt of an input of the IQ data including the amplitude information and the phase information, the separating function 210 is configured to output the phase data including the phase information and IQ data including the amplitude information and the phase information. Similarly to the first embodiment, the IQ data stored in the buffer memory 103 is an example of the first ultrasound data.

The noise reducing function 213 is configured to receive an input of the IQ data and to output noise-reduced IQ data. Similarly to the first embodiment, the noise reducing function 213 according to the present embodiment is configured to obtain the noise-reduced IQ data, by inputting the IQ data to the trained model 90.

Similarly to the first embodiment, the trained model 90 is a model that has been trained by implementing a method of deep learning or the like, while a plurality of pieces of input ultrasound data are kept in correspondence with a plurality of pieces of training ultrasound data.

The noise-reduced IQ data is data having an SN ratio higher than that of the IQ data. In the present embodiment, the noise-reduced IQ data is an example of the second ultrasound data.

Although the noise-reduced IQ data includes the amplitude information and the phase information, there is a possibility that these pieces of information may have been altered due to the noise reducing process. In the present embodiment, the expression "there is a possibility that the information may have been altered" means that the information has not necessarily been altered, but includes the situation where the quality of the information is not guaranteed.

On the basis of the amplitude information in the noise-reduced IQ data and the phase information in the IQ data, the reconstructing function 212 is configured to reconstruct phase-restored IQ data including the amplitude information and the phase information. Alternatively, because the reconstructing function 212 does not use the phase information in the noise-reduced IQ data, the data input to the reconstructing function 212 may be noise-reduced envelope data that includes only the amplitude information from the noise-reduced IQ data.

The phase-restored IQ data is data obtained by performing a noise reducing process and subsequently restoring the phase information to a pre-alteration state. The phase-restored IQ data is an example of the third ultrasound data according to the present embodiment.

The Doppler processing function 215 is configured to extract the movement information based on the Doppler effect of a moving object in a ROI set within a scanned region, by performing a frequency analysis on the phase-restored IQ data. The Doppler processing function 215 according to the present embodiment is configured to perform a blood flow detecting process to detect the direction and the magnitude (power) of a blood flow, on the basis of the amplitude information and the phase information in the phase-restored IQ data. The blood flow detecting process is an example of the process that uses the amplitude information and the phase information in the third ultrasound data according to the present embodiment.

As a method for detecting the blood flow from the phase-restored IQ data, it is possible to adopt a publicly-known color flow mapping method by which a blood flow can be detected from IQ data. The Doppler processing function 215 is configured to store blood flow data detected from the phase-restored IQ data, into the raw data memory 104. For example, the blood flow data is Doppler data representing blood flow information estimated by using the color flow mapping method.

Alternatively, the separating function 210, the noise reducing function 213, and the reconstructing function 212 of the present embodiment may be included in the Doppler processing function 215.

Next, a flow in processes performed by the separating function 210, the noise reducing function 213, and the reconstructing function 212 will be explained with reference to FIG. 8. FIG. 8 is a chart illustrating an example of a flow in a process of generating phase-restored IQ data 1053 according to the second embodiment. In FIG. 8, processes performed by the separating function 210, the noise reducing function 213, and the reconstructing function 212 are indicated in the enclosures of the broken-line boxes.

The IQ data 1051 illustrated in FIG. 8 is IQ data corresponding to a data string of mutually the same position when ultrasound transmission/reception is performed on a plurality of scanning lines. Although FIG. 8 illustrates the process performed on the IQ data 1051 corresponding to the one data string, it is also possible to perform processes on the IQ data 1051 corresponding to a plurality of data strings, in parallel to each other.

The separating function 210 extracts an argument of complex of the complex number as the phase information, from the IQ data stored in the buffer memory 103 (step S101). The separating function 210 outputs phase data 512 including the extracted phase information.

The noise reducing function 213 performs the noise reducing process that uses the trained model 90, on the IQ data stored in the buffer memory 103 (step S102) and outputs noise-reduced IQ data 1052.

The reconstructing function 212 extracts absolute values from the noise-reduced IQ data 1052 as amplitude information (step S103) and reconstructs the phase-restored IQ data 1053 from the extracted amplitude information and the phase information in the phase data 512 (step S104). As a method for the reconstruction, it is possible to adopt the calculation presented in Expression (3), similarly to the first embodiment.

The phase-restored IQ data 1053 is subsequently used in the blood flow detecting process performed by the Doppler processing function 215 (step S105).

Returning to the description of FIG. 6, the B-mode processing function 214 according to the present embodiment is configured to generate data (B-mode data) in which signal intensities are expressed with brightness levels, by performing a logarithmic compression process or the like on the IQ data 1051 stored in the buffer memory 103. The B-mode processing function 214 is configured to store the generated B-mode data into the raw data memory 104.

The image generating function 116, the display controlling function 117, and the system controlling function 118 have the same functions as those in the first embodiment. For example, the image generating function 116 is configured to generate two- or three-dimensional color doppler image data in which the blood flow information is expressed in a picture, from two-dimensional Doppler data generated by the Doppler processing function 215.

As explained above, the ultrasound diagnosis apparatus 1 according to the present embodiment includes the reconstructing function 212 configured to reconstruct the phase-restored IQ data 1053 including the amplitude information and the phase information, on the basis of the amplitude information in the noise-reduced IQ data 1052 and the phase information in the IQ data 1051. Consequently, when the ultrasound diagnosis apparatus 1 according to the present embodiment is used, it is possible to perform the blood flow detecting process that uses the amplitude information and the phase information, even after the noise reducing process that has the possibility of altering the phase information in the IQ data 1051.

When the ultrasound diagnosis apparatus 1 according to the present embodiment is used, because it is possible to use the phase-restored IQ data 1053 having a higher SN ratio realized by the noise reduction for the blood flow detecting process, it is possible to enhance the image quality of the color Doppler image data generated through the color flow mapping process.

First Modification Example

In the first embodiment described above, the example was explained in which the ultrasound diagnosis apparatus 1 performs the process of generating the compounded IQ data 53; however, for example, the external device 30 connected to the ultrasound diagnosis apparatus 1 may be configured to perform the process. When this configuration is adopted, processing circuitry of the external device 30 includes the separating function 110, the compounding function 111, the reconstructing function 112, and the noise reducing function 113.

Further, the external device 30 may include the same functions as those of the ultrasound diagnosis apparatus 1 according to the second embodiment. For example, processing circuitry of the external device 30 may include the separating function 210, the noise reducing function 213, the reconstructing function 212, and the Doppler processing function 215. The external device 30 is an example of the image processing apparatus according to the present modification example.

Second Modification Example

In the second embodiment above, the example was explained in which the processing circuitry 108 of the ultrasound diagnosis apparatus 1 includes the functions different from those in the first embodiment. However, the processing circuitry 108 may include the functions of both the first embodiment and the second embodiment. For example, at the time of performing an ultrasound examination using the B-mode processing, the same processes as those in the first embodiment may be performed. In contrast, at the time of performing an ultrasound examination using the Doppler processing, the same processes as those in the second embodiment may be performed.

Third Modification Example

In the first and the second embodiments above, the example was explained in which the reconstructing function 112 (212) uses the phase information separated from the IQ data 51 (1051) by the separating function 110 (210) for the reconstructing process. However, possible methods for the reconstruction are not limited to this example.

For instance, the reconstructing function 112 (212) may use the phase information in the IQ data 51 (1051) stored in the buffer memory 103, for the reconstructing process.

Fourth Modification Example

In the first and the second embodiments above, the noise reducing process using the trained model 90 was explained as an example; however, it is also acceptable to adopt a noise reducing process using other methods. For example, in the first and the second embodiments, it is also acceptable to use a noise reducing process that uses a mathematical model or the like.

Fifth Modification Example

In the first embodiment, the noise reducing process was used as an example of the process that uses both amplitude information and phase information. In the second embodiment, the blood flow detecting process was used as an example the process that uses both amplitude information and phase information. However, these processes are merely examples. The first and the second embodiments may include any of other processes that use both amplitude information and phase information.

The various types of data handled in the present disclosure are, typically, digital data.

According to at least one aspect of the embodiments described above, it is possible to perform the process that uses both the amplitude information and the phase information, after the process by which the phase information is lost or altered.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising processing circuitry configured:
    to receive an input of first ultrasound data and to output second ultrasound data, the first ultrasound data including both amplitude information and phase information, and the second ultrasound data including amplitude information and not including phase information;
    to reconstruct third ultrasound data on a basis of the amplitude information in the second ultrasound data and the phase information in the first ultrasound data, the third ultrasound data including both amplitude information and phase information; and
    to perform a process that uses the amplitude information and the phase information in the third ultrasound data.

2. The ultrasound diagnosis apparatus according to claim 1, wherein
    the first ultrasound data is complex signal data corresponding to a plurality of frames, and
    the processing circuitry is configured to generate the second ultrasound data by compounding signal data corresponding to the plurality of frames.

3. The ultrasound diagnosis apparatus according to claim 2, wherein
the processing circuitry is configured to generate fourth ultrasound data, on a basis of the amplitude information and the phase information in the third ultrasound data, and
a Signal-to-Noise (SN) ratio of the fourth ultrasound data is higher than that of the third ultrasound data.

4. The ultrasound diagnosis apparatus according to claim 3, wherein the processing circuitry is configured to obtain the fourth ultrasound data by inputting the third ultrasound data to a trained model that has been trained with a plurality of pieces of input ultrasound data and a plurality of pieces of training ultrasound data obtained by reducing a noise component of the plurality of pieces of input ultrasound data.

5. The ultrasound diagnosis apparatus according to claim 1, wherein
the processing circuitry is configured to generate fourth ultrasound data, on a basis of the amplitude information and the phase information in the third ultrasound data, and
a Signal-to-Noise (SN) ratio of the fourth ultrasound data is higher than that of the third ultrasound data.

6. The ultrasound diagnosis apparatus according to claim 5, wherein the processing circuitry is configured to obtain the fourth ultrasound data by inputting the third ultrasound data to a trained model that has been trained with a plurality of pieces of input ultrasound data and a plurality of pieces of training ultrasound data obtained by reducing a noise component of the plurality of pieces of input ultrasound data.

7. The ultrasound diagnosis apparatus according to claim 1, wherein the processing circuitry is configured to perform a blood flow detecting process to detect a blood flow, on a basis of the amplitude information and the phase information in the third ultrasound data.

8. The ultrasound diagnosis apparatus according to claim 7, wherein the processing circuitry is configured to output the second ultrasound data upon receipt of the input of the first ultrasound data, by using a trained model that has been trained with a plurality of pieces of input ultrasound data and a plurality of pieces of training ultrasound data obtained by reducing a noise component of the plurality of pieces of input ultrasound data.

9. The ultrasound diagnosis apparatus according to claim 1, wherein the processing circuitry is configured to output the second ultrasound data upon receipt of the input of the first ultrasound data, by using a trained model that has been trained with a plurality of pieces of input ultrasound data and a plurality of pieces of training ultrasound data obtained by reducing a noise component of the plurality of pieces of input ultrasound data.

10. The ultrasound diagnosis apparatus according to claim 1, wherein
the processing circuitry is configured:
to separate phase data including phase information from the first ultrasound data; and
to reconstruct the third ultrasound data by using the amplitude information in the second ultrasound data and the phase information in the phase data.

11. The ultrasound diagnosis apparatus according to claim 1, further comprising:
a memory configured to store therein the first ultrasound data, wherein
the processing circuitry is configured to reconstruct the third ultrasound data by using the second ultrasound data and the phase information in the first ultrasound data stored in the memory.

12. An image processing apparatus comprising processing circuitry configured:
to receive an input of first ultrasound data and to output second ultrasound data, the first ultrasound data including both amplitude information and phase information, and the second ultrasound data including amplitude information and not including phase information;
to reconstruct third ultrasound data on a basis of the amplitude information in the second ultrasound data and the phase information in the first ultrasound data, the third ultrasound data including both amplitude information and phase information; and
to perform a process that uses the amplitude information and the phase information in the third ultrasound data.

13. A non-transitory computer readable medium storing a program executed by a computer, the program causing the computer to execute:
a first processing step of receiving an input of first ultrasound data and outputting second ultrasound data, the first ultrasound data including both amplitude information and phase information, and the second ultrasound data including amplitude information and not including phase information;
a reconstructing step of reconstructing third ultrasound data on a basis of the amplitude information in the second ultrasound data and the phase information in the first ultrasound data, the third ultrasound data including both amplitude information and phase information; and
a second processing step of performing a process that uses the amplitude information and the phase information in the third ultrasound data.

* * * * *